United States Patent
Chinn et al.

(10) Patent No.: US 8,849,002 B2
(45) Date of Patent: Sep. 30, 2014

(54) NOISE ROBUST DECODER FOR MULTIPLEXING READOUT CHANNELS ON AN IMAGING SENSOR ARRAY

(75) Inventors: Garry Chinn, San Mateo, CA (US); Peter D. Olcott, Stanford, CA (US); Craig S. Levin, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 81 days.

(21) Appl. No.: 13/808,063

(22) PCT Filed: Jul. 7, 2011

(86) PCT No.: PCT/US2011/001193
§ 371 (c)(1),
(2), (4) Date: Jan. 2, 2013

(87) PCT Pub. No.: WO2012/005767
PCT Pub. Date: Jan. 12, 2012

(65) Prior Publication Data
US 2013/0142409 A1    Jun. 6, 2013

(51) Int. Cl.
*G06K 9/00* (2006.01)
*G06T 11/00* (2006.01)
*A61B 6/03* (2006.01)
*A61B 6/00* (2006.01)

(52) U.S. Cl.
CPC ............. *G06T 11/003* (2013.01); *G06T 11/006* (2013.01); *A61B 6/037* (2013.01); *A61B 6/5205* (2013.01); *G06T 2211/436* (2013.01)
USPC ........................................... 382/131; 370/464

(58) Field of Classification Search
USPC .................................. 382/100, 128–132, 232
See application file for complete search history.

(56) References Cited

U.S. PATENT DOCUMENTS

| | | | |
|---|---|---|---|
| 8,179,452 B2 * | 5/2012 | Kim et al. | 348/234 |
| 8,587,307 B2 * | 11/2013 | Ying et al. | 324/309 |
| 2009/0274356 A1 | 11/2009 | Ying et al. | |
| 2010/0177972 A1 | 7/2010 | Donoho | |
| 2010/0207629 A1 | 8/2010 | Trzasko et al. | |
| 2010/0241378 A1 * | 9/2010 | Baraniuk et al. | 702/66 |
| 2011/0058719 A1 | 3/2011 | Trzasko et al. | |
| 2011/0109773 A1 | 5/2011 | Dekel | |
| 2011/0142339 A1 | 6/2011 | Singh et al. | |

OTHER PUBLICATIONS

Lustig et al. (2007) Compressed sensing MRI. http://www.stanford.edu/~mlustig/CSMRI.pdf.

(Continued)

*Primary Examiner* — Shefali Goradia
(74) *Attorney, Agent, or Firm* — Lumen Patent Firm

(57) ABSTRACT

Compressed sensing (CS) estimation approaches rely on a priori sparsity to significantly reduce the number of samples needed to provide high sampling fidelity, relative to the normal Shannon-Nyquist limit. Accordingly, CS approaches are of considerable interest for detector multiplexing in applications which have inherently sparse signals (e.g., the two correlated photon detection events in PET imaging). However, CS approaches also tend to fare poorly in the presence of noise, which has limited their applicability in practice. In this work, we show that CS estimation can be used to provide an estimate of the support of an image. This estimated support is then used as a constraint for maximum likelihood image reconstruction. This approach has robust noise performance and provides high reconstruction fidelity.

23 Claims, 6 Drawing Sheets

(56) References Cited

OTHER PUBLICATIONS

Candès et al. (2006) Robust Uncertainty Principles: Exact Signal Reconstruction From Highly Incomplete Frequency Information. IEEE Transactions on Information Theory, Vol. 52, No. 2, Feb. 2006.
Dai et al. (2009) Subspace Pursuit for Compressive Sensing Signal Reconstruction. IEEE Transactions on Information Theory, vol. 55, No. 5, May 2009.
Blumensath et al. (2009) Iterative hard thresholding for compressed sensing. Appl. Comput. Harmon. Anal. 27 (2009) 265-274.
Needell et al. (2009) CoSaMP: Iterative signal recovery from incomplete and inaccurate sample. Appl. Comput. Harmon. Anal. 26 (2009) 301-321.
Bub et al. (2010) Temporal Pixel Multiplexing for simultaneous high-speed high- resolution imaging. Nat Methods. Mar. 2010; 7(3): 209-211. doi:10.1038/nmeth.1429.

\* cited by examiner

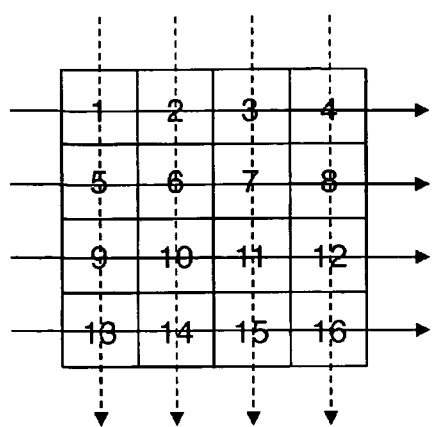
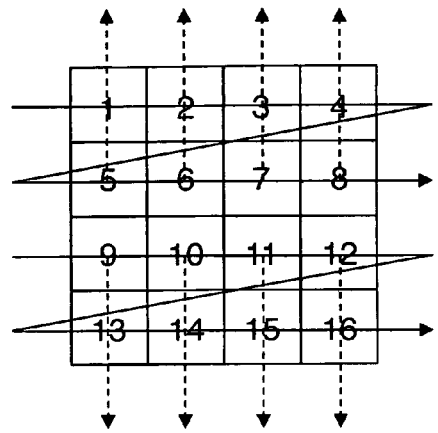
Fig. 3a     Fig. 3b
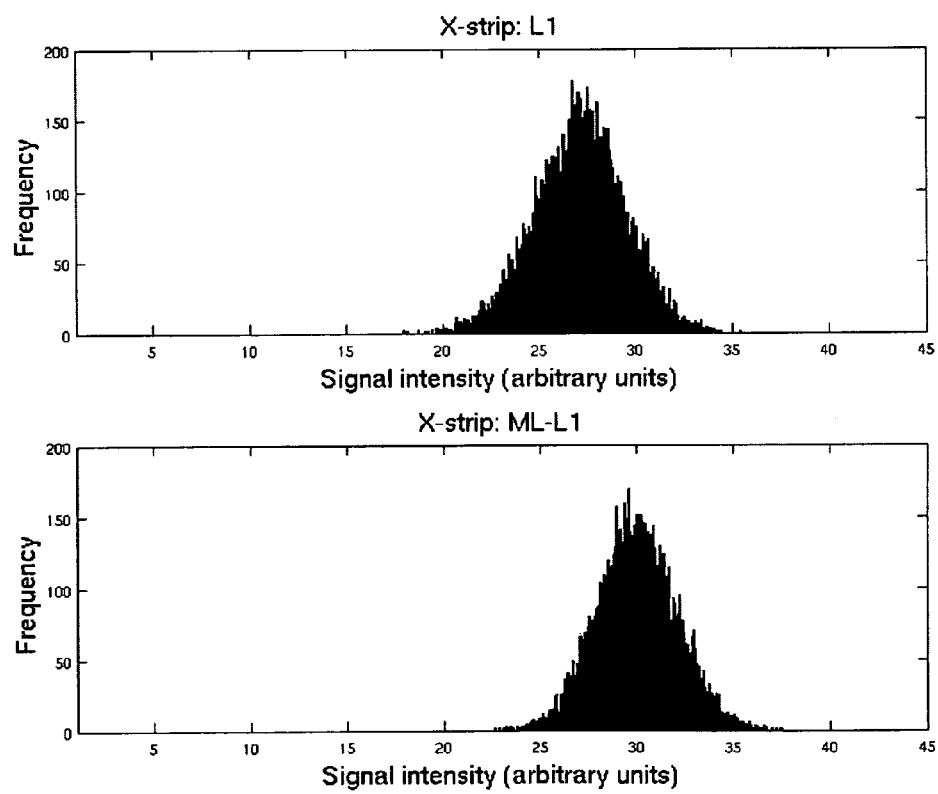
Fig. 4

Logical mapping for Pixel #10

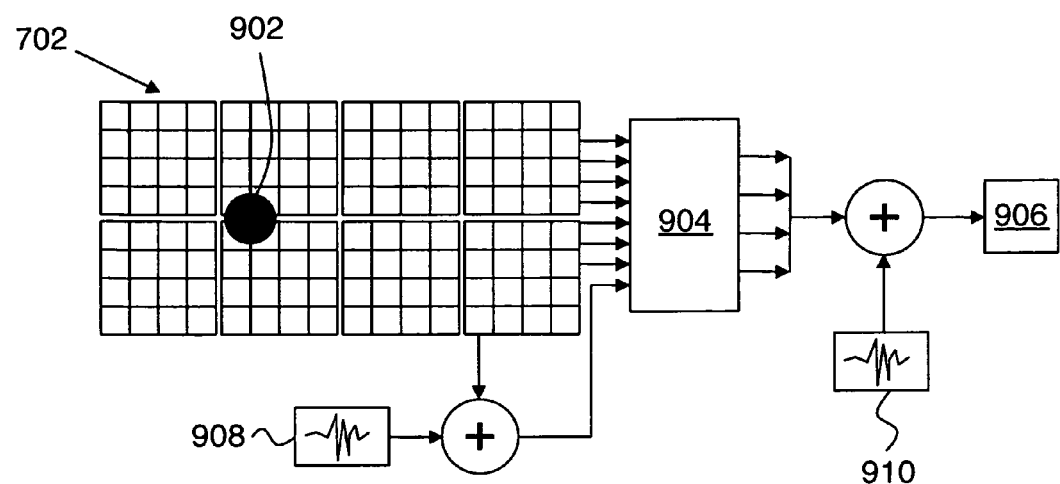
Fig. 9
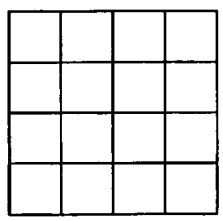 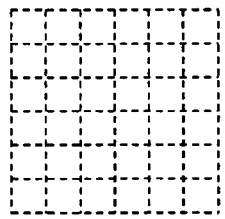 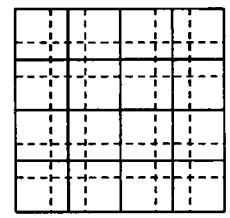
Fig. 10a  Fig. 10b  Fig. 10c
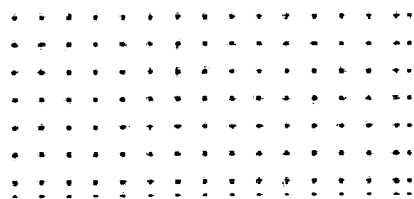 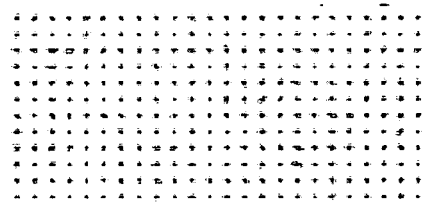
Fig. 11a  Fig. 11b

NOISE ROBUST DECODER FOR MULTIPLEXING READOUT CHANNELS ON AN IMAGING SENSOR ARRAY

STATEMENT OF GOVERNMENT SPONSORED SUPPORT

This invention was made with Government support under contracts CA119056 and CA120474 awarded by the National Institutes of Health. The Government has certain rights in this invention.

CROSS-REFERENCE TO RELATED APPLICATIONS

This application is a 371 of PCT Patent Application PCT/US2011/001193 filed Jul. 7, 2011, which claims the benefit of U.S. Application 61/399162 filed Jul. 7, 2010.

FIELD OF THE INVENTION

This invention relates to reconstruction of images from raw data.

BACKGROUND

Detector arrays for imaging frequently have a large number of detector elements, each element having its own output. However, this straightforward architecture often proves problematic in practice, because detector arrays often have a large number of detector elements, and the correspondingly large number of outputs can increase cost and complexity. Multiplexing can reduce the number of channels—lowering the cost by reducing the number of connections or components used to implement the network. Accordingly, multiplexing detector array outputs (such that there are fewer outputs than detector array elements) is of great interest, and has been extensively investigated.

Time multiplexing can be employed, where pixel elements are read out sequentially over a single channel as opposed to being read out in parallel over numerous channels. However, this approach undesirably reduces the frame rate.

In general, sampling refers to any approach for creating a digital signal from an analog signal. For an imaging array, conventional sampling theory suggests that the number of samples be on the order of the number of pixels. However, if it is known a priori that the image is sparse in some domain, the number of samples required can be significantly reduced. Techniques that exploit this kind of sparsity are often referred to as compressed sensing (CS) approaches. Other terms that have been used for this general idea include compressed sampling, compressive sampling, compressive sensing, etc. However, CS approaches unfortunately tend to perform poorly in the presence of noise, which can significantly limit the practical application of CS methods.

Accordingly, some workers are considering modifications of the normal CS approach in an attempt to improve performance. One example is the work of Trzasko et al. (US 2011/0058719), where conventional image reconstruction (e.g., a low resolution image) is used to provide an estimate of the spatial support of the image. CS image reconstruction is then performed using this spatial support estimate as a priori information for the CS image reconstruction.

However, it remains challenging to realize the theoretical benefits of CS approaches in the presence of noise.

SUMMARY

CS approaches could be used for the detector array multiplexing problem, since CS theory suggests that the required number of readout channels may be much smaller than the number of detector pixels, especially for inherently sparse images such as nuclear medicine imaging or very high-speed or low-light optical imaging. However, thus far CS has not been considered for such application because of the above-described difficulties at low SNR.

We have found, surprisingly, that the theoretical advantages of CS approaches can often be realized in the presence of significant noise by following a three part process as indicated on FIG. 1. First, a preliminary image is computed from raw data using compressed sensing (step 102). Here, compressed sensing is broadly regarded as any linear estimation approach that relies on a priori sparsity or finding sparse solutions to underdetermined linear systems of equations. As indicated above, the quality of this preliminary image may be poor in the presence of noise. Second, the support of the preliminary image is computed (step 104). Here, support is to be understood from a numerical computation perspective. Ideally, the support of an image would be all pixels having non-zero values. Realistically, the support is defined as all pixels of the image having pixel value magnitudes greater than a predetermined threshold (pixels falling below this threshold are deemed negligible). Determination of such thresholds for zero testing is commonplace in numerical computation, and is therefore not described further here. The result of this step is a support constraint—i.e., further processing takes this support estimate to be a priori support information.

The third step 106 is computing a final image from the raw data using maximum likelihood estimation combined with the support constraint. Unexpectedly, this approach has been found to provide superior results, even though it appears that substantial information is being thrown away (e.g., the relative amplitude information for all pixels in the support of the preliminary image). It is convenient to refer to the present approach as an ML-CS approach.

Here, the three steps are described separately for convenience of exposition. In practice, they may be combined. For example, a single method may be employed to provide a support estimate from raw data using compressed sensing, thereby combining steps 102 and 104.

More specifically, an imaging system according to an embodiment of the invention can include a set of detector pixels connected to a set of output channels, where there are fewer output channels than detector pixels. Detector pixels may be any photodetector element, including but not limited to: charge coupled devices (CCD), CMOS sensors, silicon photomultipliers (SiPM), photomultiplier tubes (PMT), avalanche photodiodes (APD), and Geiger-mode APD. For example, the detector pixels can be micro-cell Geiger pixels of a silicon photomultiplier. These photodetectors may also be coupled to other optics such as lenses, image intensifiers, or scintillation crystals. Also in non-limiting example, a silicon photomultiplier is made of up individual micro-cells, and therefore each silicon photomultiplier can be configured as an imaging array. Lastly, another non-limiting example of an imaging array is an array of solid-state detectors that receive high-energy radiation in the form of X-rays and Gamma rays. These solid state detectors can have an electrode pattern deposited on a material like cadmium-zinc-telluride (CZT) solid-state high energy photon detector that defines the imaging detectors.

A processor in the system can be configured to: 1) receive raw data from the output channels, 2) compute a preliminary image from the raw data using compressed sensing, 3) compute a support of the preliminary image to provide a support constraint, and 4) compute a final image from the raw data using maximum likelihood estimation combined with the support constraint. The final image can be provided as an output. Further channel reduction can be realized by applying time multiplexing techniques to the spatially multiplexed channels. Suitable time multiplexing techniques of encoding detector signals are described in Levin, et al. (US 2010/0258731), hereby incorporated by reference in its entirety.

Similarly, a method according to an embodiment of the invention can include the following steps: 1) receiving raw data from an imaging system having fewer output channels than detector pixels, 2) computing a preliminary image from the raw data using compressed sensing, 3) computing a support of the preliminary image to provide a support constraint, 4) computing a final image from the raw data using maximum likelihood estimation combined with the support constraint, and 5) providing the final image as an output.

In preferred embodiments, a multiplexing network can be included that connects each detector pixel to distinct output channel subsets. Preferably, the multiplexing network connects each detector pixel to the same number of output channels (i.e., the multiplexing is obtained by implementing a constant weight code). The multiplexing network can include one or more distinct intermediate levels, each level having its corresponding inputs and outputs where multiplexing of the detector pixels to the output channels is provided by a combination of the multiplexing levels. For example, multiplexing N detector pixels to M output channels can proceed directly in a single N:M multiplexing layer, or in two layers (N:A multiplexing followed by A:M multiplexing), or in three layers (N:A, followed by A:B, followed by B:M) etc.

In cases where intermediate multiplexing layers are employed, it is preferred that each of the multiplexing layers connects each of its inputs to the same number of its outputs (i.e., each multiplexing layer is obtained by implementing a constant weight code). The code weight can be the same in each layer or different in some or all of the multiplexing layers.

It is also preferred that the code be sparse to minimize the number of connections between the detector pixels and the output channels. A sparse code is defined as the column entries containing zeros for more than half the entries.

Preferably, the codes corresponding to the multiplexing network have maximum sum of the distances between the output channel subsets corresponding to any two of the detector pixels. More precisely, let D be the distance between the two output channel subsets corresponding to any pair of pixels. The codes are preferably selected to maximize the sum of all D over all pairs of output channel subsets, e.g. maximize the sum of all distances between columns of the sensing matrix. In this description of an embodiment of the invention, the Hamming distance is used as the distance function. However, any distance function that satisfies the properties of a metric space distance may be used. A metric space distance function is any function that satisfies the following three properties: Symmetry, Positive-Definiteness and the Triangle inequality. Let a distance function be defined as a function $F(A,B)$, where A and B are column vectors of a compressed sensing matrix (or any other mapping matrix). The symmetry property is expressed as $F(A,B)=F(B,A)$. The positive-definiteness property is expressed as $F(A,B)>=0$, and $F(A,B)=0$, if and only if $A=B$. The triangle inequality property is expressed as $F(A,C)<=F(A,B)+F(B,C)$ for any three points A, B, and C. These properties of metric space distance functions are well known in the art. Examples of valid metric space distance functions include, but are not limited to: Hamming distance, Euclidean distance, Chebyshev distance, Lee distance, and Block distance.

It is expected that the use of such codes in connection with detector pixel multiplexing may be useful independently of how signals are processed. Accordingly, an embodiment of the invention is an imaging system including: 1) a set of detector pixels connected to a set of output channels, where there are fewer output channels than detector pixels, and 2) a multiplexing network that connects each detector pixel to a distinct output channel subset; where the multiplexing network is configured to implement a sparse code having maximum distance between the output channel subsets corresponding to any two of the detector pixels. A preferred embodiment of the sparse code is a binary constant-weight code where the distance metric is the Hamming distance.

The present approach is compatible with light sharing, where the number of detector pixels is less than the number of scintillator crystals. Light sharing can be beneficial to increase spatial resolution without increasing the number of detector pixels.

In some case, we can assume an imaging system has an input-output relation given by $y=Cx+e$, where y is a raw data vector, x is a detector pixel output vector, C is the sensing matrix (C can also be referred to as the multiplexing matrix), and e is additive noise. The detector pixel output vector x can be partitioned into a signal vector s and pixel noise vector n. A noteworthy feature of this model is that it has two noise sources (i.e., n and e). Conventional image recovery approaches tend to not account properly for the pixel noise (i.e., n), and only account for the output additive noise e.

Computing the preliminary image can include computing a norm-constrained vector $x_1$ such that $Cx_1=y$. The norm constrained vector $x_1$ can have minimal $l_1$ norm. Alternatively, the norm constrained vector $x_1$ can have minimal $l_0$ norm. Any other norm constraint suitable for CS image can also be employed, including but not limited to: minimization of penalized versions of the $l_0$ and $l_1$ norm and constrained $l_0$ and $l_1$ norm minimization. Computing the final image can include: 1) partitioning x into signal and noise vectors s and n respectively such that s corresponds to the support of $x_1$ and n corresponds to the negligible components of $x_1$, and 2) performing maximum likelihood estimation of s.

This approach is applicable to a wide range of imaging applications, ranging from medical imaging to digital cameras. The present approach is especially beneficial for reducing the cost of high-resolution and/or high-speed imaging applications. Such applications are common in medical imaging, and include planar imaging by X-rays or nuclear medicine, magnetic resonance imaging (MRI), X-ray computed tomography (CT), positron emission tomography (PET), and single photon emission computed tomography (SPECT). This approach will also benefit three dimensional imaging such as time-of-flight cameras being developed as next generation user interfaces for game controllers and light detection and ranging (LIDAR). Other potential applications include high-speed optical imaging with digital cameras, low-light optical imaging with digital cameras, and time-of-flight imaging for medical and non-medical applications.

This approach provides significant advantages. Decoding in this manner is more robust to noise than previous methods and is computationally feasible to implement. Other noise robust methods exist but tend to be either less robust to noise and/or too computationally intensive to implement, particularly in high-resolution imaging arrays. For positron emission tomography, we have performed simulations showing that this approach can improve the SNR of the decoded signal by 3-4 times relative to conventional compressed sensing techniques on compressed sensing multiplexing topologies. The decoder can also be applied to conventional multiplexing topologies to provide a 50% decoded SNR improvement over conventional multiplexing decoders. While preserving a minimum necessary recovered signal-to-noise ratio, cost can be lowered by enabling multiplexing under noisy conditions. Compressed sensing matrices and the preferred decoder also allow our imaging system to compensate for a few "bad" pixels by improving the yield of high-resolution digital cameras or arrays of detector pixels.

BRIEF DESCRIPTION OF THE DRAWINGS

FIGS. 3a-b show examples of cross-strip multiplexing.

FIG. 4 shows results of a comparison of the present approach to a conventional approach for $l_1$ norm minimization combined with cross-strip multiplexing.

FIG. 9 show a noise and illumination model suitable for use in connection with embodiments of the invention.

FIGS. 10a-c show an example of three-to-two coupling for light sharing where the number of scintillation crystals is greater than the number of detector pixels.

FIGS. 11a-b show simulated flood images for one-to-one coupling and for three-to-two coupling.

DETAILED DESCRIPTION

In the following sections, two specific examples of the preceding principles are considered. In the first example, the use of compressed sensing to provide a support constraint for maximum likelihood image recovery (ML-CS) is considered in connection with positron emission tomography (PET). In the second example, the use of constant-weight codes for multiplexing PET detector pixel elements is considered in connection with ML-CS image recovery.

A) Compressed Sensing (CS) to Provide a Support Constraint for Maximum Likelihood (ML) Image Recovery A1) CS Model In this section, we consider a PET detector built from scintillator crystal pixels that are individually coupled one-to-one to silicon photomultipliers (SiPM). A description of the symbols used to describe the mathematical model is shown in Table 1.

TABLE 1

| Symbol | Description |
| --- | --- |
| x | d × 1 SiPM analog output signal vector |
| y | m × 1 digital channel signal vector |
| s | s × 1 sparse digital channel signal vector |
| n | (d − s) × 1 multiplexed noise vector |
| e | m × 1 channel noise vector |
| C | m × d multiplexing weight coefficients |
| P | m × d permutation matrix |
| A | m × s map of sparse signal components |
| B | m × (s − d) map of noise |

Compressed sensing is especially interesting for application to PET imaging because PET detector signals have a sparse representation in the natural basis. The natural basis corresponds to the pixels of a 2-D detector array. For PET, most of the signal for any annihilation photon is concentrated in very few detector pixels. CS employs non-adaptive linear projections that preserve the underlying signal information at a lower sampling rate than Shannon-Nyquist theory. From these projections, optimization algorithms can be used to decode the original set of detector signals.

Figure 1:
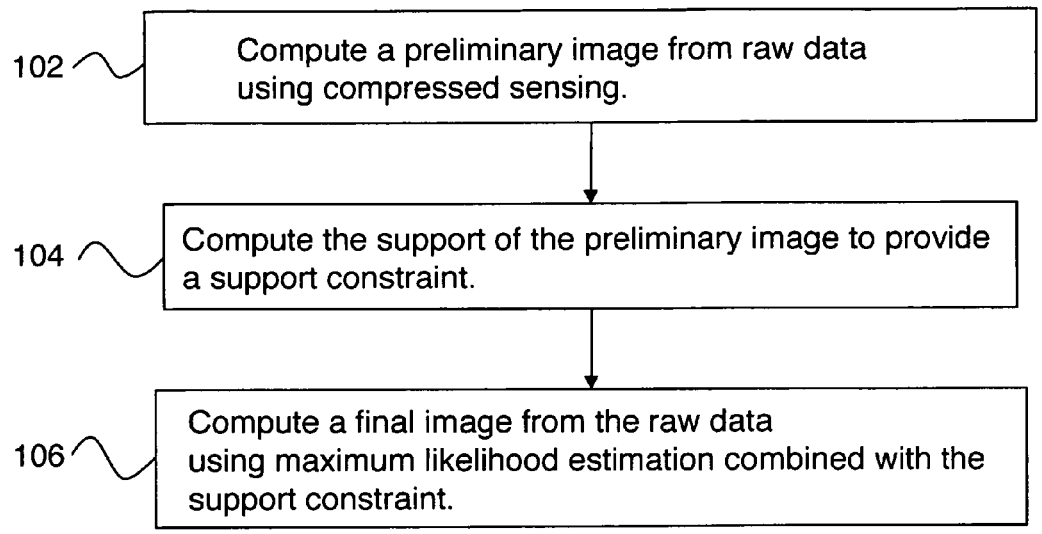
FIG. 1 shows method steps of an embodiment of the invention.
Figure 2:
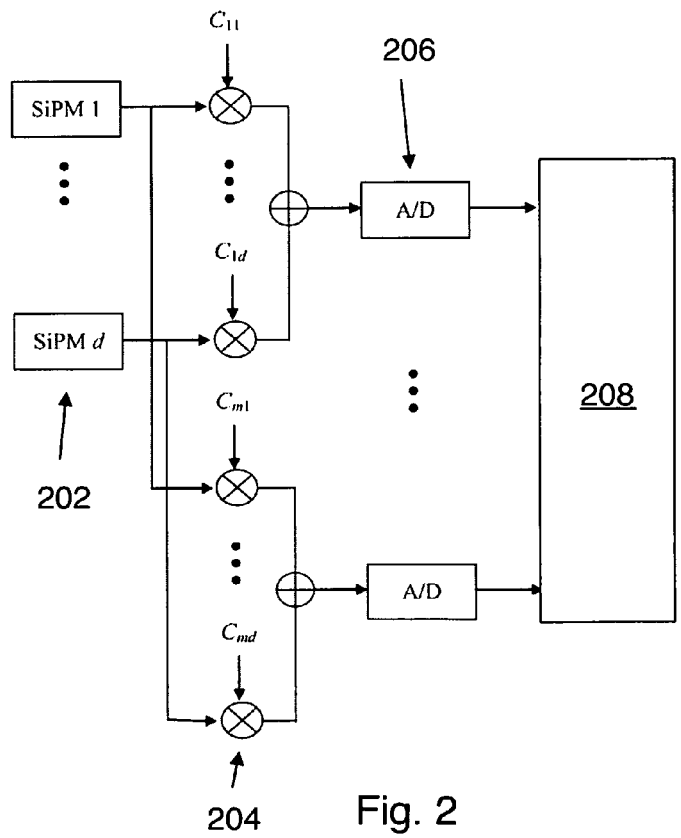
FIG. 2 shows a system according to an embodiment of the invention.

Each detector block forms a 2-D array of pixels. Let the d individual SiPM pixels of the detector block be denoted by a d by 1 vector x. Multiplexed detector readouts can be used to read this 2-D array of SiPM pixels as shown in FIG. 2.

In this example, a set of SiPM detector pixels 202 is coupled to a set of output channels 206 with a multiplexing network 204. There are fewer output channels than detector pixels. The multiplexing network can provide weighted sums of the detector pixel signals as output channels by various analog and/or digital methods. Preferably, analog methods such as resistive or capacitive networks are employed. The coefficients of the weights are represented in the matrix C. The vector y is the vector of output channel signals. Preferably, each output channel is digitized by an analog-to-digital converter (A/D). The output channels 206 are provided as inputs to a processor 208 which implements various methods as described below. Practice of the invention does not depend critically on whether processor 208 is implemented in hardware, software, or any combination thereof.

Let the number of readout channels m of the detector be denoted by the m by 1 vector y. Then we may describe the detector readout as $$y = Cx + e \quad (1)$$

where the matrix C is the m×d sensing matrix and e is a random measurement noise vector.

Because x is already sparse in the 2-D spatial domain, there is no need for a sparsifying basis representation. In compressed sensing theory, C must satisfy the restricted isometry property, as is known in the art. By Shannon-Nyquist sampling theory, the number of readout channels m=d, which corresponds to non-multiplexed readout with one readout channel per SiPM detector pixel. From CS theory, it is known that only m≥2s readout channels are needed where s≤d/2 is the desired maximum number of photon events that can be resolved in a single detector block within a selected time window. For coincidence detection, typically s=2 and by CS theory, an entire PET system could be theoretically compressed to only 4 readout channels.

The d SiPM pixel signals can be decoded by $l_0$ norm minimization $$\hat{x}_0 = \arg\min\|x'\|_0, y = Cx'. \quad (P0)$$

It has been shown that the $l_0$ norm solution is closely approximated by the $l_1$ norm minimization $$\hat{x}_1 = \arg\min\|x'\|_1, y = Cx'. \quad (P1)$$

CS theory provides methods for minimizing the sampling rate. However, there is no guarantee that the SNR of the signals will be acceptable. When the signal is oversampled, m>2s, it is theoretically possible to improve the SNR of the decoded detector signals. However, CS theory does not provide optimal SNR solutions in the presence of noise. Therefore, in the present approach $l_0$ norm or $l_1$ norm minimization can be employed to estimate the support of the signal for constrained maximum likelihood decoding of spatially multiplexed detector readout signals. The support of a signal corresponds to the indices of the non-zero pixels (or pixels having non-negligible amplitude relative to a predetermined threshold). Thus, the CS calculation is only used to provide an estimate of the support to use as a constraint in subsequent maximum likelihood image reconstruction.

A2) ML Decoding

To decode multiplexed detector signals with optimal SNR, let the support of x, $S=\{S_i\}=\text{supp}(\hat{x}_0)$ or $S=\{S_i\}=\text{supp}(\hat{x}_1)$ for i=1Ks where s=|S| (size of set S), be found by solving (P0) using the iterative hard thresholding (IHT) algorithm or by solving (P1) using the alternating direction method (ADM). The ADM and IHT methods are both known in the art. IHT uses a non-linear modification to Landweber iterations and is computationally more efficient than ADM.

We can form a permutation matrix $$P = [e_{j(i)}], \; e_{j(i)} = \begin{cases} j(i) = S_i & i \leq s \\ j(i) = S^C_{i-s} & s < i \leq d \end{cases}$$

and apply to Eqn. (1) to yield $$y = [A \; B]\begin{bmatrix} s \\ n \end{bmatrix} + e \quad (2)$$

$$[A \; B] = CP^T, \; \begin{bmatrix} s \\ n \end{bmatrix} = Px$$

where s represents the s by 1 sparse signal vector. We assume that the zero (or negligible) components of $\hat{x}_1$ are noise and these components are represented by the (d−s) by 1 detector noise pixel vector n. The m by s matrix A maps the signal vector s to y while the m by (d−s) matrix B maps the noise pixels to y.

The optimal SNR solution can be recovered by constructing a likelihood model with Eqn. (2). For independent identically distributed Gaussian noise pixels n, the maximum likelihood solution to (2) is given by $$\hat{s} = (A^T R^{-1} A)^{-1} A^T R^{-1} y$$

$$R = BE[nn^T]B^T + E[ee^T] \quad (3)$$

Other noise models such as Poisson distributed noise or Gaussian-Poisson mixtures could also be used in this framework with an alternate method for maximizing the likelihood function such as an iterative gradient approach.

A3) Sensing Matrices

CS theory can be used to create many different multiplexing topologies. We present two of the many possible topologies for electronic multiplexing schemes for the SiPM pixel array: 1) a standard "2-projection function" also known as "cross-strip" readout (see FIGS. 3a-b) and 2) a random, uniformly distributed basis sampled from the discrete cosine transform (DCT) matrix (not shown), which by CS theory, is a good candidate for a multiplexing topology. In DCT multiplexing, each channel corresponds to weighted sums of pixels with weights corresponding to the DCT coefficients.

In cross-strip multiplexing, several pixel values are summed into row and column channels. In the example of FIG. 3a, the 16 pixels of a 4×4 imaging array are reduced to 4 row signals (solid lines) and 4 column signals (dashed lines). In the example of FIG. 3b, the 16 pixels are reduced to 2 row signals (solid lines) and 8 column signals (dashed lines). These multiplexing concepts can be applied to larger arrays.

Sensing matrices formed by either technique can be used to recover multiple interaction events with high probability. There are degenerate cases where it is not possible to correctly resolve the positions of the multiple interactions. By carefully designing the sensing matrix and selecting the multiplexing ratio, these degenerate cases can be kept to an acceptably small percentage of the total number of events. Cross strip multiplexing is easier to implement because all of the pixels are given the same weight in any readout channel. However, the multiplexing ratio, the ratio of the number of pixels to the number of readout channels, cannot be chosen arbitrarily because the number of readout channels is equal to the number of rows plus the number of columns in the logical array. For partial DCT sensing matrices, the implementation is more difficult because the matrix is dense and continuous weights are used to form each readout channel. However, partial DCT sensing matrices enable an arbitrary multiplexing ratio. This allows greater flexibility to tradeoff readout SNR for cost/complexity.

A4) Results

We simulated a 511 keV photon randomly positioned on an 8×8 imaging array. We performed 10,000 trials of the photon producing 1, 2, and 3 interactions with equally distributed energy. Random Gaussian-distributed pixel noise was added to all 64 pixels. We compared a 16-channel, 8×8 cross strip readout against a 16-channel, partial DCT weighted 16-channel readout using $l_0$ norm and $l_1$ norm minimization and the present approach of maximum likelihood compressed sensing decoding of a set of detector pixel signals (Eqn. 3).

FIG. 4 shows the histograms of $l_1$ norm minimization (top) and ML–$l_1$ norm minimization (bottom) for 8×8 cross-strip multiplexing. The true signal value had amplitude of 30 and a variance of 1. ML–$l_1$ norm minimization improves the mean square error by 54% through a reduction in bias.

Figure 5:
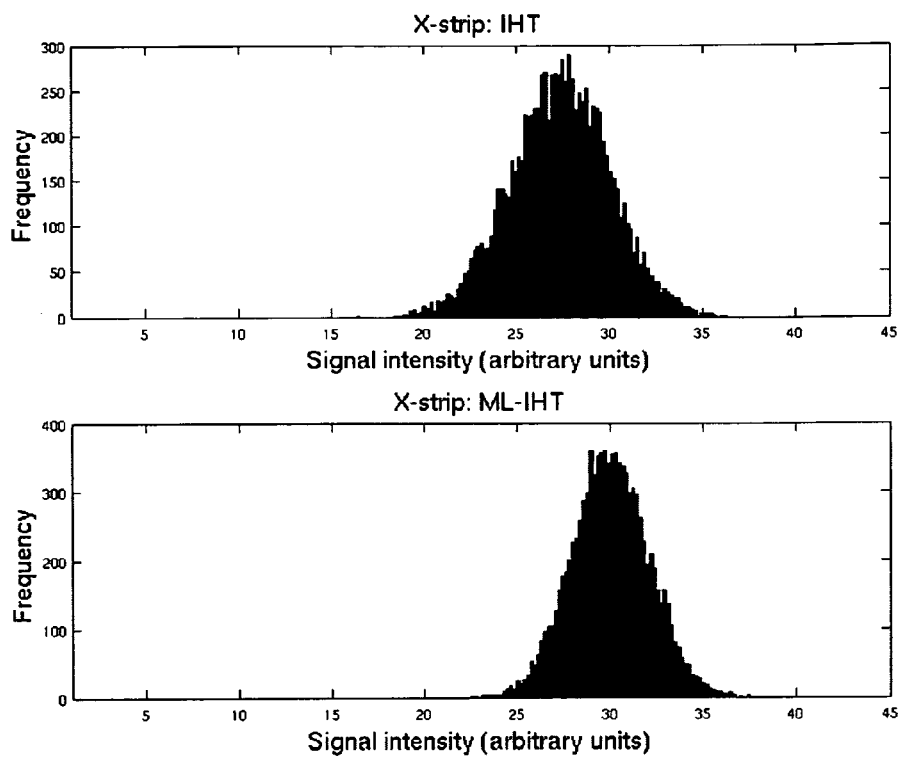
FIG. 5 shows results of a comparison of the present approach to a conventional approach for $l_0$ norm minimization combined with cross-strip multiplexing.

FIG. 5 shows the histograms for 8×8 cross-strip multiplexing using IHT (top) and ML–IHT (bottom). Both are cases of $l_0$ norm minimization. The true signal value had amplitude of 30 and a variance of 1. The present ML–IHT approach reduces the mean square error by up to 3%.

Table 2 summarizes the mean square error (MSE) for cross-strip multiplexing for the various signal recovery methods. ML estimation reduces the MSE for all cases. ML–$l_1$ is the most accurate of all approaches with a 53% reduction of MSE compared to $l_1$ norm minimization for single interaction events. The least amount of improvement was observed for 3-interaction events. There was a small difference between ML–IHT and IHT of no more than 3% in MSE.

TABLE 2

Mean square error for 16-channel cross-strip multiplexing

| Pixel hits | Signal recovery algorithm | | | |
|---|---|---|---|---|
| | $l_1$ | ML-$l_1$ | IHT | ML-IHT |
| 1 | 14.0 ± 0.1 | 6.57 ± 0.01 | 32.2 ± 0.2 | 31.2 ± 0.2 |
| 2 | 83.8 ± 1.4 | 75.1 ± 1.1 | 88.1 ± 1.6 | 88.9 ± 1.6 |
| 3 | 59.5 ± 0.7 | 54.6 ± 0.6 | 56.1 ± 0.6 | 55.5 ± 0.6 |

Figure 6:
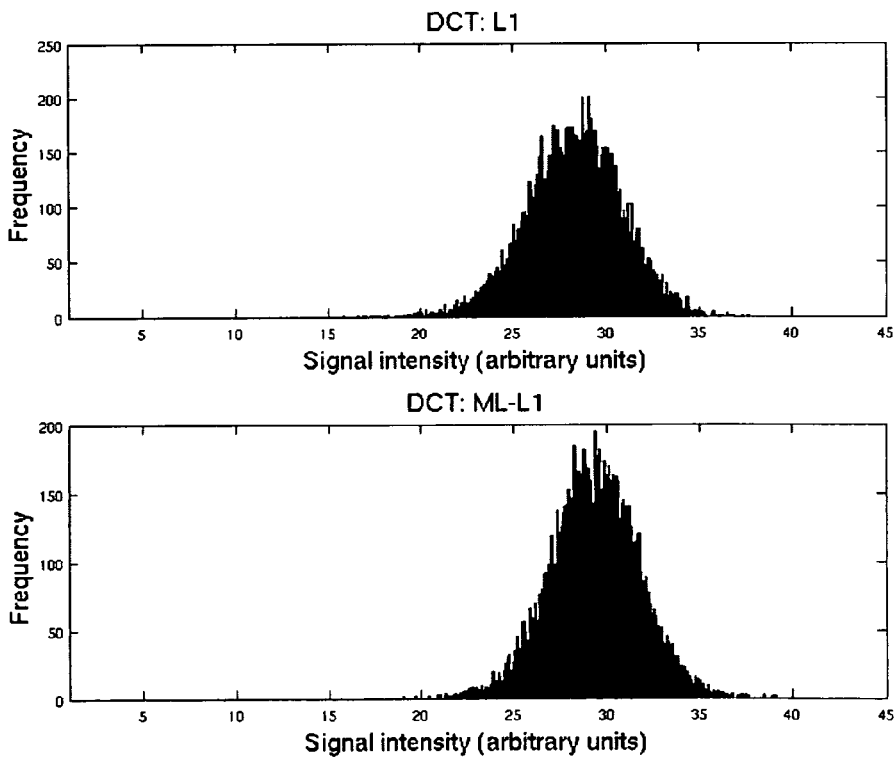
FIG. 6 shows results of a comparison of the present approach to a conventional approach for $l_0$ norm minimization combined with discrete cosine transform multiplexing.

FIG. 6 shows the histograms for partial DCT multiplexing using IHT (top) and ML-IHT (bottom) with a photopeak signal of 30 and variance of 1. The bias is similar, but the variance is reduced by the ML estimation. Table 3 summarizes the MSE for partial DCT multiplexing. ML-IHT recovers signals with a 56% lower MSE for single interaction events. There was no statistically significant difference for 3-interaction events.

TABLE 3

Mean square error for 16-channel DCT multiplexing

| Pixel hits | NSignal recovery algorithm | |
|---|---|---|
| | IHT | ML-IHT |
| 1 | 11.9 ± 0.1 | 5.25 ± 0.01 |
| 2 | 36.0 ± 0.3 | 33.9 ± 0.2 |
| 3 | 44.3 ± 0.4 | 44.0 ± 0.4 |

The positioning accuracy is shown in Table 4. The percentages of events that are exactly positioned are compared for cross-strip multiplexing and partial DCT multiplexing. An accuracy of 100% indicates that all events were positioned on the correct pixel and no additional positioning blurring is introduced by multiplexing. Positioning errors lead to blurring. The results do not consider other positioning blurring that occur within the crystals, only positioning blurring caused by readout multiplexing. Partial DCT multiplexing more accurately positions the events for 1, 2, and 3 interaction cases.

TABLE 4

Percentage of events exactly positioned on pixel

| Pixel hits | Multiplexing method | |
|---|---|---|
| | Cross-strip | Partial DCT |
| 1 | 98% | 100% |
| 2 | 64% | 87% |
| 3 | 49% | 60% |

A5) Conclusions

We have developed a new framework for multiplexing PET detector readouts and developed a new method for optimal SNR decoding. For example, any previously developed multiplexing scheme such as Anger logic could be described in terms of a sensing matrix and the optimal ML positioning algorithm could be produced.

Compressed sensing methods can be used to recover signals for any multiplexing scheme. We demonstrate that both cross-strip and partial DCT multiplexing with $l_0$ and $l_1$ norm minimization signal recovery can resolve multiple interactions in an array of detector pixels. We also showed that $l_0$ and $l_1$ norm minimization can find the signal support for constrained ML estimation. This approach allows the underlying signal noise model to be used to improve the accuracy of signal recovery. More generally, it is expected that any other norm-constraint such as penalized $l_0$ and $l_1$ norm minimization or constrained $l_0$ and $l_1$ norm minimization (see for instance Zhang et al, User's Guide for YALL1: Your Algorithms for L1 Optimization for some examples of penalized and constrained $l_1$ norm minimization) that is useful for CS would also be applicable to the present ML-CS approach.

Finally, we showed that DCT multiplexing using the best signal recovery method ML-IHT yielded a 20-55% reduction in MSE for 1-3 interaction events compared to cross-strip multiplexing using ML-$l_1$ (the best signal recovery method for cross-strip multiplexing). This demonstrates that multiplexing by compressed sensing topologies can offer superior performance than conventional spatial multiplexing as used in standard detector readout schemes.

B) Constant Weight Codes

B1) CS Model

As described above, compressed sensing is a method to reconstruct a signal, sampled by an underdetermined linear system, using a priori knowledge that it can be sparsely represented or be compressible. In this section we consider PET block detectors that use compressed sensing to significantly reduce the number of readout (ADC) channels, while also preserving the underlying energy, spatial, and time resolution. More specifically, we have implemented a compressed sampling network that includes an array of silicon photomultiplier (SiPM) pixels that are uniquely connected to a smaller array of preamplifiers. The array of preamplifiers is then uniquely encoded into a smaller array of readout channels. This two layer multiplexing network or linear mapping network can uniquely identify the location of the event, energy, and timing. In designs that use light-sharing, all SiPM pixels in the light cone of a scintillation event are uniquely decoded. The approach presented here uses CS techniques to recover the exact magnitude of the light detected at each pixel unlike traditional linear positioning methods that simply generate the total magnitude and average position of the light produced at all pixels.

Here we consider a PET detector that is built from a large, 128 element SiPM pixel array that is either one-to-one coupled with 128 scintillation crystal elements, or in a 3:2 light-sharing design with 196 scintillation crystal elements. Light-sharing is preferable to increase the spatial resolution of the detector while not increasing the number of SiPM detector pixels.

Following the CS theory as given above, we may then describe the detector readout as:

$$y=C(s+n)+e \qquad (4)$$

Here y is the output vector from the multiplexing network, C is the CS matrix, s is the detector pixel output vector (which is to be estimated from y), n is the additive noise at each of the SiPM pixels, and e is the additive noise in the output channels. Using the support of the signal as described above, we can decompose Eqn. 4 into:

$$y = [A \ B]\begin{bmatrix} s \\ n \end{bmatrix} + e \qquad (5)$$

After determining the support of the signal s and calculating the noise covariance matrix R from B, $$R=BE[nn^T]B^T+E[ee^T] \qquad (6)$$

we define a reconstruction matrix W:

$$W=(A^T R^{-1} A)^{-1} A^T R^{-1} \qquad (7)$$

The optimal SNR solution for reconstructing the pixel value ŝ is:

$$\hat{s}=Wy \qquad (8)$$

Once ŝ is reconstructed, the position of ŝ is known from the support, and the spatial position can be estimated as:

$$\text{Event position } [x, y] = \frac{\sum_i s_i \cdot \vec{P}[i]}{\sum_i s_i} \quad (9)$$

where $\vec{P}[i]$ is the position of pixel i, and $s_i$ are the elements of the reconstruction vector $\hat{s}$.

B2) Constant Weight Codes as Sensing Matrices

We have found that good sensing matrices for signal multiplexing are ones that have the minimum number of coefficients per column. Since each coefficient is either a connection or a discrete component, minimizing the number of non-zero coefficients reduces both the capacitive loading of the SiPM pixels and the number of discrete components. Therefore sparse codes can be used to construct good sensing matrices. We have found a large class of matrices called constant weight codes that provide just this requirement. It will be appreciated by one skilled in the art, that other sparse codes besides constant-weight codes may be used. A weight is defined as a binary connection, either zero (no connection) or one (connection). A constant 2-weight code has 2 connections per column for all columns in the matrix. In these codes, matrices are preferably optimized so that each column in the vector has the maximum Hamming distance between any pair of columns. The Hamming distance between a pair of columns is defined as the sum of the number of ones after the XOR operation between the entries of each of row entries. Maximizing the sum of the pair-wise Hamming distance makes each column as distinguishable as possible, so that they can be later uniquely reconstructed in the presence of noise.

Sensing matrices are therefore a linear map between input detector pixels and output channels. For physical implementation of the linear map, the entries can represent linear weighting of the voltage, current, or delay of the detector signal, and summing those weighted values to a subset of the outputs. If the values are binary 1's and zeros, then the linear map is implemented by connecting or not connecting the detector pixel to the specified output.

B3) Construction of Sensing Matrices

Because of significant capacitive attenuation of the signal for SiPM devices, in one example it was preferred to employ a two level CS scheme. This example has 128 detector pixels, and it is desired to multiplex these pixels to 16 output channels. Instead of a single layer 128:16 multiplexing network, a double layer multiplexing network was employed that provided 128:40 multiplexing followed by 40:16 multiplexing. The 128:40 multiplexing was provided by a first 2-constant weight code C1. The 40:16 multiplexing was provided by a second 2-constant weight code C2.

Figure 7:
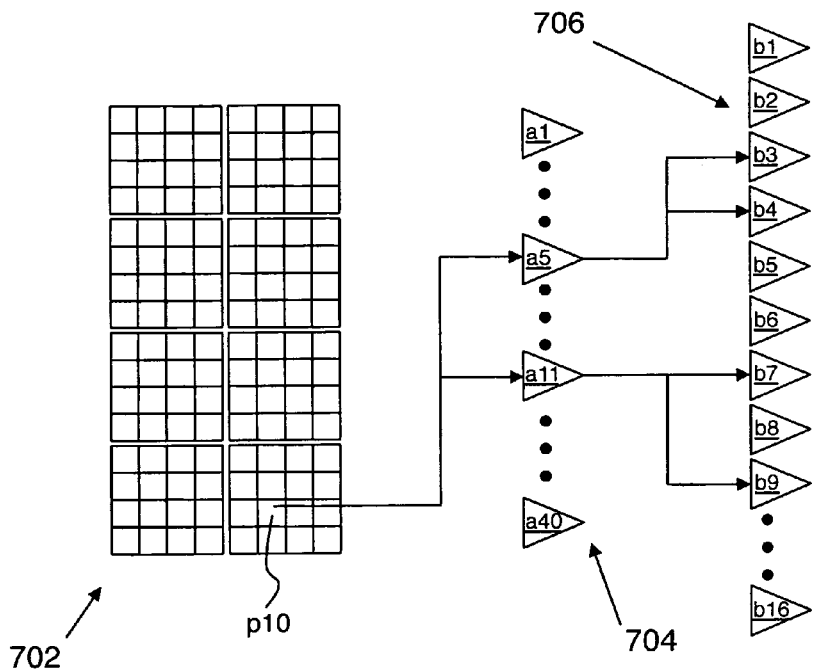
FIG. 7 shows an example of multiple-level multiplexing using constant-weight codes suitable for use with embodiments of the invention.
Figure 8A:
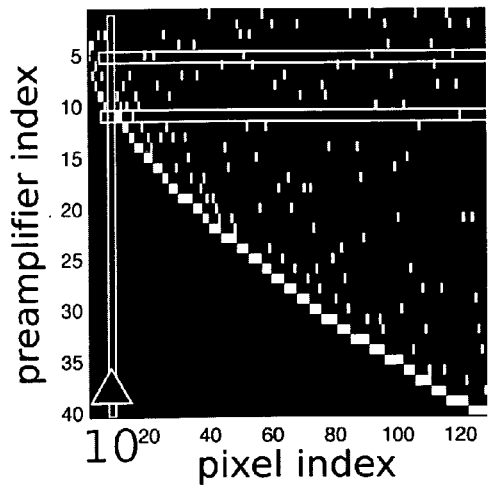
FIGS. 8a-b show code matrices for the example of FIG. 7.
Figure 8B:
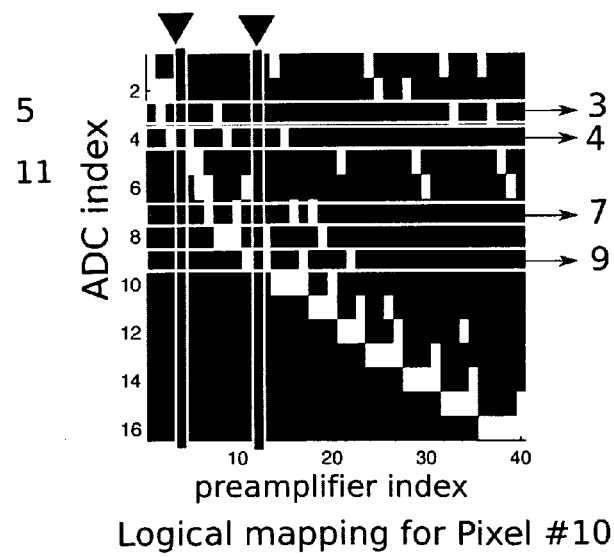

FIGS. 7 and 8a-b show this example. FIG. 8a shows the code matrix for code C1. FIG. 8b shows the code matrix for code C2. FIG. 7 shows a schematic hardware implementation, where the detector pixel array 702 is multiplexed to the output channels 706 via an intermediate layer 704. For illustrative purposes, the connections for one of the pixels of array 702 are shown (all other connections are not shown for clarity). Pixel p10 is connected to preamplifiers a5 and all of intermediate layer 704. Preamplifier a5 is connected to output channels b3 and b4. Preamplifier a11 is connected to output channels b7 and b9. Thus, pixel p10 is connected to output channels b3, b4, b7, and b9. Every pixel in array 702 is connected to a distinct pair of preamplifiers in intermediate layer 704. Similarly, every preamplifier in intermediate layer 704 is connected to a distinct pair of output channels. Thus, each pixel of array 702 corresponds to a unique set of 4 output channels. Since the codes are known, it is possible to invert this, such that signals in the output channels can be decoded to determine which pixel or pixels provided the outputs.

The two sensing matrices, a constant 2-weight 128:40 code (FIG. 8a) and a constant 2-weight 40:16 code (FIG. 8b), are specifically created to uniquely decode the maximum number of pixels firing simultaneously. Each column in the matrix has 2 connections, hence their designation as constant 2-weight codes. Equivalently, a constant weight code connects each of its inputs to the same number of outputs. Constant weight codes are used extensively for barcodes (2 of 5, 3 of 9), forward error correction codes, and many other applications in digital signal processing.

The final 4-constant weight code is derived by the multiplication of C1(128:40) with C2(40:16) to result in the final sensing matrix C(128:16). Each of the constant weight codes was calculated using a brute force heuristic search to maximize the pair wise Hamming distance between any two codes. Pixels that have been mapped to a code with a large Hamming distance can be clearly resolved from each other, even though they happen simultaneously.

B4) q-Ary Constant-weight Codes as Sensing Matrices

Another set of codes that would also be good for a CS scheme are a class of constant-weight codes called q-ary codes. Instead of a binary 1, or 0, a q-ary code consists of 0, 1, . . . up to q unique values. A constant-weight q-ary code consists of a constant number of each value. For example, a constant [2,3,2,5] 4-ary constant-weight code, has 2 1's 3 2's, 2 3's, and 5 4's per column. Q-ary codes are also sparse, since there are only a fixed number of non-zero entries per column. For a CS scheme, the number weight of the q-ary code linear maps the q-ary value times the signal magnitude to an output channel. Therefore, the same signal model, y=C(s+n)+e, is preserved, where the compressed sensing matrix C, is a q-ary constant-weight code that linearly maps the signal s, and the noise n, to the output y.

B5) Simulation of Compressed Sensing PET Block Detector

A Matlab® script was written to Monte Carlo simulate the light-shared signal of a crystal array that was uniformly irradiated. FIG. 9 shows the model. For each scintillation crystal in a block detector 702 (either one-to-one or three-to-two coupled), a light cone 902 is generated that distributes the light onto a 2×2 subset of the 128-pixel array. Uncorrelated noise 908 is added for each SiPM pixel, and is projected through the sensing matrix 904. Also, ADC noise 910 is directly added to the output 906. The event is then reconstructed, and its energy and position are then calculated.

In the three-to-two light-sharing design, sub-tiled arrays of 6×6 crystals are mapped to 4×4 arrays of SiPM detectors (e.g., as shown on FIGS. 10a-c). Here, FIG. 10a shows a 4×4 array of detector pixels, and FIG. 10b shows a 6×6 array of scintillation crystals. In a light sharing design, the 6×6 array of scintillation crystals is disposed on top of the 4×4 array of pixel elements, as shown on FIG. 10c.

The SNR for the SiPM pixel is based on the experimentally measured noise from dark counts versus the mean photo-peak signal from a 511 keV event. For illustration purposes, signal was arbitrarily set to a magnitude of 100, and variance was set to 1. Also, for each ADC, a variance of 1 was added. We compared the SNR of the recovered mean signal for a 128:16 compressed sensing design (factor of 8 reduction) versus a 128:24 cross-strip multiplexed design (5.33 factor reduction). We analyzed the ability to position all of the crystals in the CS design.

B6) SNR Analysis of Compressed Sensing Versus Cross-Strip Multiplexed PET Detector The events were then reconstructed, the sum energy was calculated, positioned, and 2-D histogrammed. FIG. 11a shows simulation results for one to one coupling of an 8×16 scintillation crystal array to an 8×16 detector pixel array. FIG. 11b shows simulation results for 3:2 coupling of an 12×24 scintillation crystal array to an 8×16 detector pixel array. The scintillation crystals were resolved for both 1:1 and 3:2 designs.

Figure 12:
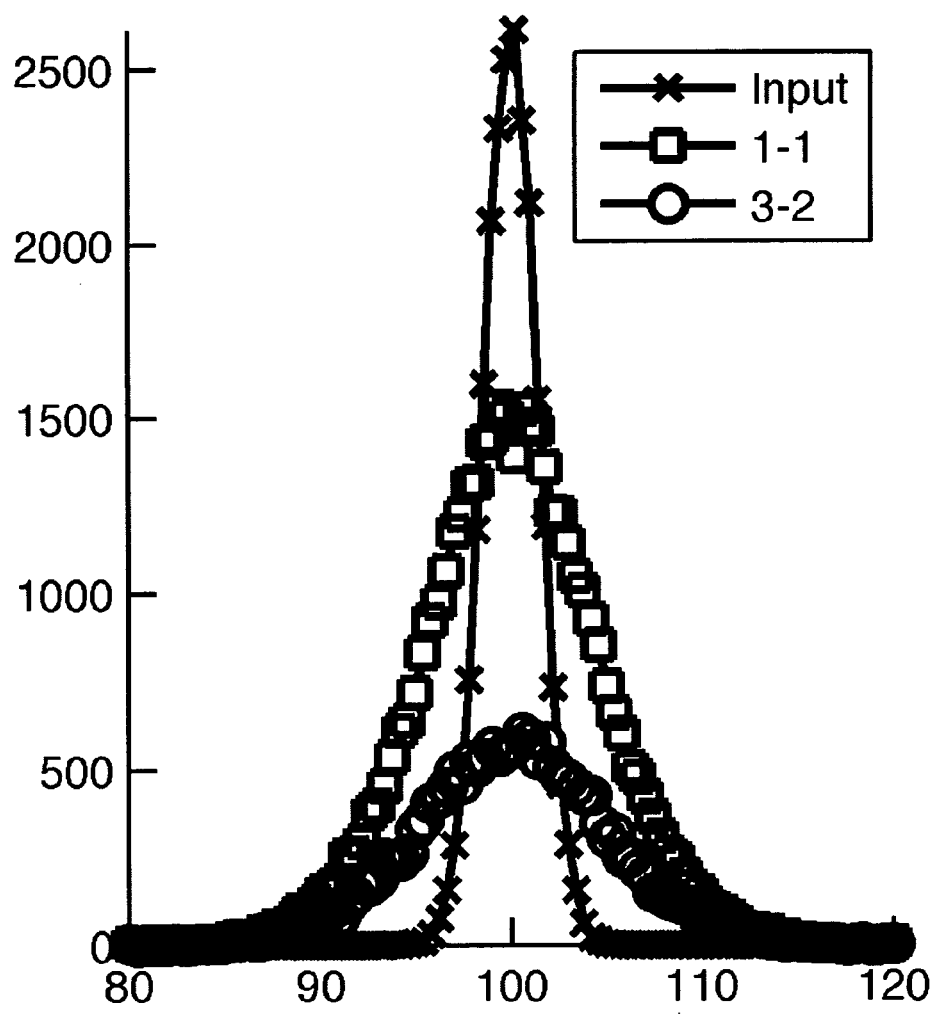
FIG. 12 shows SNR results for one-to-one coupling and for three-to-two coupling.

For one-to-one coupled designs where a single pixel is reconstructed, we calculated a 30.6±0.1 dB SNR for CS-ML, and a 30.7±0.1 dB SNR for conventional cross-strip multiplexing. For designs where 3:2 light-sharing occurs, we calculated a 26.1±0.1 dB SNR for CS-ML, and a 28.0±0.1 dB SNR for conventional cross-strip multiplexing. The input SNR was taken to be 37 dB (from SNR=20 $\log_{10}$ (511 keV peak location/$\sigma_{dark\ counts}$)). FIG. 12 shows these results. The SNR improvement for the cross-strip 3:2 light-sharing design is from the lower multiplexing ratio (5.33 versus 8).

B7) Conclusion

We have developed a compressed sensing framework that can be used to multiplex large area SiPM-based scintillation detectors for PET. Using a two-level compression matrix, we were able to resolve a 12×24 array of scintillation crystals that were mapped to an 8×16 array of SiPM pixels using only 16 ADC readout channels.

C) Delay Encoding

In the previous examples, the CS scheme uses a linear mapping matrix C 204 that is either 0, 1 or some set of magnitudes, and this linearly maps the signal s to a set of outputs y 208. Instead, we can describe the signal s 202, as s(t), as a function of time. Then instead of modulating the magnitude of the signal s, we can, based on the sensing matrix C, uniquely delay the signal s(t) to an output y(t). Any method of implementing delays can be used such as physical delay elements, either as longer wires, or filters that delay the signal by a deterministic amount of time. The entries in the CS matrix C, would either, not delay (a value of zero), delay (with a time delay of 1 unit of time), or in a q-ary code, delay with a unit of q(with a time delay of q units of time). It will be appreciated by one skilled in the art, that both schemes can be advantageously combined, therefore, C=C_magnitude*C_delay, so both amplitude and time modulation can be used for imaging arrays.

A motivation to use delays is that we have an ADC converter 206 of a fixed sampling frequency F. By forming uniquely encoded time shifted copies of the signal s, and uniquely encoding these signals to a plurality of signals y, these signals y can then be digitized by a fixed frequency ADC 206 of frequency F, and a reconstructed signal $\hat{x}$ can be of a higher sampling frequency than the Nyquist rate of the ADCs 206 sampled at a frequency F. The time interleaved sampling of signals using delays that are encoded from a binary, or q-ary constant-weight code or CS matrix, can therefore be used to synthesize a much higher effective sampling rate, and can be used to encode a multitude of detector signals into a fewer set of ADCs.

The invention claimed is:

1. An imaging system comprising:
a set of detector pixels connected to a set of output channels, wherein there are fewer output channels than detector pixels; and a processor configured to:
receive raw data from the output channels;
compute a preliminary image from the raw data using compressed sensing;
compute a support of the preliminary image to provide a support constraint;
compute a final image from the raw data using maximum likelihood estimation combined with the support constraint; and
provide the final image as an output.

2. The system of claim 1, further comprising a multiplexing network that connects each detector pixel to distinct output channel subsets.

3. The system of claim 2, wherein the multiplexing network includes one or more distinct multiplexing levels, each multiplexing level having its corresponding inputs and outputs, and wherein multiplexing of the detector pixels to the output channels is provided by a combination of the multiplexing levels.

4. The system of claim 2, wherein the multiplexing network is configured to implement a sparse code having a maximum pair-wise sum of the distance between the output channel subsets corresponding to any two of the detector pixels.

5. The system of claim 2, wherein a mapping between the detector pixels and the output channels is performed by delays encoded by the multiplexing network.

6. The system of claim 1, wherein the imaging system includes a system selected from the group consisting of: medical imaging systems, magnetic resonance imaging systems, X-ray computed tomography systems, positron emission tomography systems, ultrasound imaging systems, and single photon emission computed tomography systems.

7. An imaging method comprising:
receiving raw data from an imaging system having fewer output channels than detector pixels;
computing a preliminary image from the raw data using compressed sensing;
computing a support of the preliminary image to provide a support constraint;
computing a final image from the raw data using maximum likelihood estimation combined with the support constraint; and
providing the final image as an output.

8. The method of claim 7, wherein the computing a support of the preliminary image comprises applying a threshold to determine which elements of the preliminary image to include in the support, and which elements of the preliminary image are negligible.

9. The method of claim 7, wherein the raw data comprises a raw readout vector y, wherein C is a sensing matrix, x=s+n is a detector pixel output vector, s is a signal vector, n is a noise vector, and e is additive noise, and wherein the imaging system has an input-output relation given by y=C(s+n)+e.

10. The method of claim 9, wherein the computing a preliminary image comprises computing a norm-constrained vector $x_1$ such that $Cx_1$ =y.

11. The method of claim 10, wherein the norm constrained vector $x_1$ has minimal $l_1$ norm or has minimal $l_0$ norm.

12. The method of claim 10, wherein the norm constrained vector $x_1$ is a constrained or penalized combination of $l_0$ norm and $l_1$ norm solutions.

13. The method of claim 10, wherein the computing a final image comprises:
partitioning x into signal and noise vectors s and n respectively such that s corresponds to the support of $x_1$ and n corresponds to the negligible components of $x_1$; and
performing maximum likelihood estimation of s.

14. An imaging system comprising:
- a set of detector pixels connected to a set of output channels, wherein there are fewer output channels than detector pixels;
- a multiplexing network that connects each detector pixel to a distinct output channel subset;
- wherein the multiplexing network is configured to implement a sparse code having maximum pair-wise sum of the distances between the output channel subsets corresponding to any two of the detector pixels.

15. The system of claim 14 wherein the multiplexing network is configured to implement a sparse code that is a binary or q-ary constant-weight code.

16. The system of claim 14 wherein the multiplexing network is configured to implement a sparse code that is a hierarchical concatenation of sparse codes.

17. The system of claim 14 wherein the multiplexing network is configured to use delays based on the sparse code.

18. The system of claim 14 wherein the multiplexing network uses continuous-valued analog signals.

19. The system of claim 14 wherein the multiplexing network uses multiplication of binary weights to output digital signals.

20. The system of claim 14 wherein the detector pixels are Geiger-mode pixels.

21. An imaging method comprising:
- receiving raw detector signals from an array of detector pixels;
- computing a sparse code having maximum pair-wise sum of distances;
- using the sparse code to multiplex the raw detector signals to a set of output channels according to a linear map.

22. The method of claim 21, wherein the sparse code includes a hierarchical concatenation of sparse sub-codes.

23. The method of claim 21, wherein the linear map uses delay to encode the raw detector signals to the output channels.

* * * * *